(12) United States Patent
Bohn et al.

(10) Patent No.: US 6,528,271 B1
(45) Date of Patent: *Mar. 4, 2003

(54) INHIBITION OF βARRESTIN MEDIATED EFFECTS PROLONGS AND POTENTIATES OPIOID RECEPTOR-MEDIATED ANALGESIA

(75) Inventors: Laura M. Bohn, Durham, NC (US); Fang-Tsyr Lin, Durham, NC (US); Marc G. Caron, Hillsborough, NC (US); Robert J. Lefkowitz, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,554

(22) Filed: Dec. 22, 1999

Related U.S. Application Data

(63) Continuation-in-part of application No. 09/233,530, filed on Jan. 20, 1999, now Pat. No. 6,110,693, which is a continuation of application No. 08/869,568, filed on Jun. 5, 1997, now Pat. No. 5,891,646.

(51) Int. Cl.$^7$ .................. C07K 14/00; C07K 17/00; C12Q 1/00; G01N 33/53; G01N 33/567

(52) U.S. Cl. ................ 435/7.2; 435/4; 530/350

(58) Field of Search .............. 424/9.1, 9.2; 435/4, 435/7.2; 530/350

(56) References Cited

U.S. PATENT DOCUMENTS

| | | | |
|---|---|---|---|
| 5,591,618 A | 1/1997 | Chantry et al. | 435/194 |
| 5,597,699 A | 1/1997 | Lanzara | 435/7.21 |
| 5,658,783 A | 8/1997 | Grandy et al. | 435/325 |
| 5,661,184 A | 8/1997 | Helton et al. | 514/574 |
| 5,821,067 A | 10/1998 | Grandy et al. | 435/7.2 |
| 5,882,944 A | 3/1999 | Sadee | 436/501 |
| 5,891,646 A * | 4/1999 | Barak et al. | 435/7.2 |
| 6,007,986 A | 12/1999 | Sadée | 435/6 |
| RE36,547 E | 2/2000 | Crain et al. | 514/282 |
| 6,028,175 A | 2/2000 | Grandy et al. | 530/350 |
| 6,087,115 A | 7/2000 | Gershengorn et al. | 435/7.21 |
| 6,096,756 A | 8/2000 | Crain et al. | 514/282 |
| 6,103,492 A | 8/2000 | Yu | 435/69.1 |
| 6,110,693 A * | 8/2000 | Barak et al. | 435/7.2 |

FOREIGN PATENT DOCUMENTS

| | | |
|---|---|---|
| WO | WO98/55635 | 12/1998 |

OTHER PUBLICATIONS

Bohn, Laura M., *Enchanced Morphine Analgesia in Mice Lacking β–Arrestin 2*, Science, (Washington D.C.), vol. 286, No. 5449, Dec. 24, 1999, pp. 2495–2498.

Chen, Jeannie, et al., *Increased Susceptibility to Light Damage in an Arrestin Knockout Mouse Mode of Oguchi Disease (Stationary Night Blindness)*, Investigative Ophthalmology & Visual Science, vol. 40, No. 12, Nov. 1999, pp. 2978–2982.

Kovoor, Abraham, et al., *μ and σ Opioid Receptors Are Differentially Desensitized by the Coexpression of β–Adrenergic Receptor Kinase 2 and β–Arrestin 2 in Xenopus Oocytes*, The Journal of Biological Chemistry, (U.S.A.), vol. 272, No. 44, Oct. 31, 1997, pp. 27605–27611.

Mathier, Michael, A. et al., *Enhanced Left Ventricular Contractile Responses to Acute β–Adrenergic Stimulation in a β–Arrestin 1 Knockout Mouse*, Scientific Sessions of the American Heart Assoiciation, Orlando, Florida, US, vol. 96, No. 8, Suppl, 1997, XP–000983952, p. I–445.

Schulz, Rüdiger, et al., *Phosducin, β–arrestin and Opioid receptor migration*, European Journal of Pharmacology, vol., 375, No. 1–3, Elsevier Science B.V., Jun. 30, 1999, pp. 349–357.

Whistler, Jennifer, L., et al., *Morphine–activated opioid receptors elude desensitization by β–arrestin*, Proceedings of the National Academy of Sciences of the United States, vol. 95, No. 17, Aug. 18, 1998, pp. 9914–9919.

Zhang, Je, et al., *Role of G protein–coupled receptor kinase in agonist–specific regulation of $_\mu$–opioid receptor responsiveness*, Proc. Natl. Acad. Sci. USA, vol. 95, pp. 7157–7162 (Jun. 1998).

Yu, Yunkai, et al., $_\mu$–*Opioid Receptor Phosphorylation, Desensitization, and Ligand Efficacy*, the Journal of Biological Chemistry, vol. 272, No. 46, pp. 28869–28874 (1997).

Nestler, Eric J., *Under Siege: The Brain on Opiates*, Neuron, vol. 16, pp. 897–900 (May 1996).

Keith, Duane E., et al., *Morphine Activates Opioid Receptors without Causing Their Rapid Internalization*, The Journal of Biological Chemistry, vol. 271, No. 32, pp. 19021–19024 (1996).

Cox, Brian M., *Mechanisms of Tolerance, Opiods in Paid Control: Basic and Clinical Aspects*, Ch. 6, pp. 109–130 (1999).

Sternini, Catia, et al., *Agonist–selective endocytosis of $_\mu$opioid receptor by neurons in vivo*, Proc. Natl. Acad. Sci. USA, vol. 93, pp. 9241–9246 (Aug. 1996).

* cited by examiner

Primary Examiner—Anne-Marie Baker
(74) Attorney, Agent, or Firm—Burns, Doane, Swecker & Mathis, L.L.P.

(57) ABSTRACT

The present invention provides a βarrestin knockout mouse useful for screeening compounds for efficacy in controlling pain, methods of controlling pain in subjects by inhibiting binding of βarrestin to phosphorylated μ opioid receptors, and methods of screening a compound for activity in potentiating μ opioid receptor agonist activity (e.g., morphine activity) by determining whether or not said compound inhibits βarrestin binding to a phosphorylated μ opioid receptor.

12 Claims, 3 Drawing Sheets

INHIBITION OF βARRESTIN MEDIATED EFFECTS PROLONGS AND POTENTIATES OPIOID RECEPTOR-MEDIATED ANALGESIA

This application is a continuation-in-part of U.S. application Ser. No. 09/233,530, now issued as U.S. Pat. No. 6,110,693, filed Jan. 20, 1999; which is a continuation of U.S. application Ser. No. 08/869,568, now issued as U.S. Pat. No. 5,891,646, filed Jun. 5, 1997.

This invention was made with Government support under NIH grant numbers NS 19576 and HL16037. The Government has certain rights to this invention.

FIELD OF THE INVENTION

The present invention concerns transgenic mice useful for screening compounds for their ability to control pain, methods of controlling pain in subjects in need thereof, methods of screening a compound for activity in controlling pain, and/or screening compounds for opioid receptor agonist activity.

BACKGROUND OF THE INVENTION

G protein coupled receptors (GPCRs) have important roles in mediating fundamental physiological processes such as vision, olfaction, cardiovascular function, and pain perception. Cellular communication through GPCRs requires the coordination of processes governing receptor activation, desensitization, and resensitization. However, the relative contribution of desensitization mechanisms to the overall homeostatic process still remains largely unexplored in vivo. GPCR kinases (GRKs) act to phosphorylate activated receptors and promote their interaction with βarrestins. This, in turn, prevents further coupling with G proteins and disrupts normal activation of the second messenger signaling cascade. By this mechanism, GRKs and βarrestins can act to dampen GPCR signaling, thereby leading to desensitization of the receptor (S. Ferguson, et al., *Annu Rev Biochem* 67, 653 (1998)). At least six GRKs (GRK1–6) and four arrestins (visual and cone arrestin, βarrestin-1 and -2) have been discovered; however, the functional significance of such redundancy is unclear.

Overexpression or inactivation of certain GRKs leads to modulation of receptor responsiveness (W. Koch, et al., *Science* 268, 1350 (1995); H. Rockman et al., *Proc Natl Acad Sci USA* 93, 9954 (1996); D. Choi et al. *J Biol Chem* 272, 17223 (1997); G. Iaccarino et al., *Am J Physiol* 275, H1298 (1998); K. Peppel, et al., *J Biol Chem* 272, 25425 (1997); H. Rockman, et al., *J Biol Chem* 273, 18180 (1998). J. Walker et al., *Am J Physiol* 276, R 1214 (1999)). In addition, mice that are deficient in βarrestin-1 display increased cardiac contractility in response to β-adrenergic receptor agonists (D. Conner et al., *Circ Res* 81, 1021 (1997)).

SUMMARY OF THE INVENTION

Pain perception (nociception) is mediated by a cascade of events from the point of the stimulus to integrative circuits in the brain. Nociception involves signals that are mediated by several classes of receptors and signal transduction mechanisms such as GPCRs for substance P, opioid peptides, etc. and ion channels such as NMDA receptors. Antinociception has been known for more than 1000 years to be induced by the alkaloid compound, morphine, which functions as an agonist at the μ opioid receptor. The activity of agonists for signaling through GPCRs is usually limited by cellular mechanisms that dampen the signal of the agonist, a process referred to as desensitization. These mechanisms include phosphorylation of agonist-activated receptors by specific receptor kinases called GRKs followed by the interaction of the phosphorylated GPCR with any of the members of the arrestin family of proteins. Morphine-mediated antinociception is known to wane with time, however the contribution of the desensitization is controversial and for all practical purposes is unknown. With the βarrestin knockout mice disclosed herein, it is shown that interfering with (eliminating) one of the key protein components of the desensitization mechanism greatly enhances the potency and efficacy of the antinociceptive properties of morphine.

Accordingly, a first aspect of the present invention is a knockout mouse useful for testing the efficacy of potential analgesic agents, the cells of said mouse containing at least one inactive endogenous βarrestin gene (preferably the βarrestin-2 gene), the mouse exhibiting a phenotype of decreased sensitivity to pain after administration of a μ opioid receptor agonist such as morphine as compared to the corresponding wild type mouse. The mouse may be heterozygous or homozygous for the inactive endogenous βarrestin gene. The mouse is useful for evaluating potential analgesic drugs, and particularly for evaluating the contribution of the desensitization mechanisms to the antinociceptive effects of endogenous opioids.

A second aspect of the invention is a method of controlling pain in a subject. The method comprises inhibiting βarrestin binding to the phosphorylated μ opioid receptor in said subject in an amount effective to induce or enhance analgesia in the subject. The method may be carried out with or without concurrently administering a μ opioid receptor agonist (typically an opiate such as morphine) to said subject.

A third aspect of the present invention is a method of screening a compound for activity in potentiating μ opioid receptor agonist activity (e.g., morphine activity). The method comprises determining whether or not the compound inhibits βarrestin binding to a phosphorylated μ opioid receptor. The inhibition of such binding by the compound indicates the compound is active in potentiating μ opioid receptor agonist activity.

A particular aspect of the present invention is a method of screening a compound for activity in controlling pain. The method comprises determining whether or not the compound inhibits βarrestin binding to phosphorylated μ opioid receptor. The inhibition of such binding by the compound indicates the compound is active in controlling pain (i.e., is a candidate compound for controlling pain, and should be subjected to further screening and testing for pain control). Any degree of inhibition may be examined, with greater inhibition of binding indicating potentially greater activity of the compound being tested.

Further aspects of the present invention include compounds produced or identified by the methods described hereinabove and pharmaceutical formulations of the same, along with the use of such compounds for the preparation of a medicament for the potentiation of the activity of μ opioid receptor agonists such as morphine, and/or for the control of pain, in a subject in need thereof, either alone or in combination with a μ opioid receptor agonist such as morphine.

The foregoing and other objects and aspects of the present invention are explained in detail in the drawings herein and the specification set forth below.

BRIEF DESCRIPTION OF THE DRAWINGS

FIG. 1A. Schematic diagrams of βarr2 gene (top), targeting vector (middle) and the homologous recombinant gene (bottom) (7). The arrows indicate the translational start and stop sites. The black boxes indicate the exons. A 0.8 kb Bam HI-Hind III fragment was replaced with the pGK-neo cassette such that the entire exon 2, encoding amino acids 9–19, was deleted. Transcription of the neomycin-resistant gene opposed that of the βarr2 gene. Both 5' and 3' external probes were used in genotype screening. Restriction enzyme sites are as follows: B, Bam HI; N, Nco I; H, Hind III; R, Eco RI.

FIG. 1B. Southern blot analysis of genomic DNA from wild type (WT), heterozygous (+/−) and homozygous (−/−) mice. Tail DNA was digested with Bam HI and analyzed by Southern blotting with the 5' probe as shown in (A). A 3.5-kb fragment is indicative of the βarr2 knock-out (KO) allele and a 3-kb fragment is indicative of the wild-type allele.

FIG. 1C. Protein immunoblot analysis of βarr2 expression in WT, βarr2+/−, and βarr2-KO mice. Membranes were blotted for βarr1 (top) and βarr2 (bottom) protein expression. Each lane was loaded with 25 µg protein derived from the same lysates of the indicated brain regions.

DETAILED DESCRIPTION OF THE PREFERRED EMBODIMENTS

Figure 1:
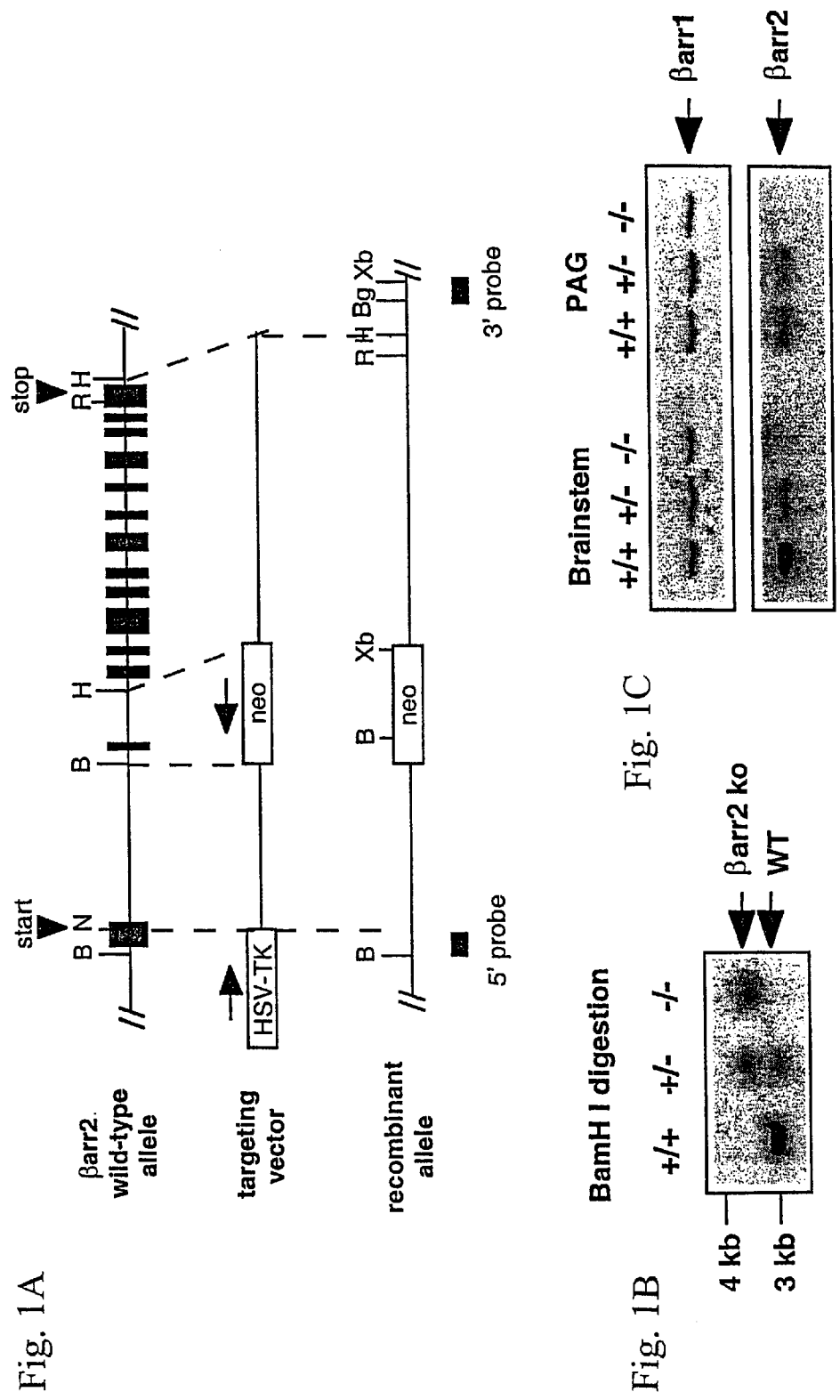
FIG. 1. Characteristics of the targeted disruption of the mouse βarrestin-2 (βarr2) gene.

The term "arrestin" as used herein has its ordinary meaning in the art and is intended to encompass all types of arrestin, including but not limited to visual arrestin (sometimes referred to as Arrestin 1), βarrestin 1 (sometimes referred to as Arrestin 2), and βarrestin 2 (sometimes referred to as Arrestin 3).

The term "βarrestin" (or "β-arrestin") as used herein is intended to encompass all types of βarrestin, including but not limited to βarrestin 1 and βarrestin 2.

The phrases "concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

The production of βarrestin knockout mice can be carried out in view of the disclosure provided herein and in light of techniques known to those skilled in the art, such as described in U.S. Pat. No. 5,767,337 to Roses et al.; U.S. Pat. No. 5,569,827 to Kessous-Elbaz et al.; and U.S. Pat. No. 5,569,824 to Donehower et al. (the disclosures of which applicants specifically intend to be incorporated by reference herein in their entirety); and A. Harada et al., *Nature* 369, 488 (1994). Particularly preferred mice for carrying out the present invention are also disclosed below.

1. Assay techniques. The step of determining whether or not βarrestin binding to the phosphorylated µ opioid receptor is inhibited by the test compound may be carried out by any suitable technique, including in vitro assay and in vivo assay (e.g., in a cell that contains the βarrestin and the phosphorylated μ opioid receptor). A particularly suitable technique for in vivo assay is disclosed in U.S. Pat. No. 5,891,646 to Barak et al. (the disclosure of which is to be incorporated by reference herein in its entirety). In general, this technique involves providing a cell that expresses μ opioid receptor as a G-protein coupled receptor, and contains the βarrestin protein conjugated to an optically detectable molecule (e.g., green fluorescent protein). The test compound is then introduced into the cell (e.g., by microinjection, by electroporation, by suspending the cell in an aqueous solution that contains the test compound, by contacting the cell to liposomes that contain the test compound, by insertion of a heterologous nucleic acid into the cell that encodes and expresses the test compound, etc.). Translocation of the molecule from the cytosol of the cell to the membrane edge of the cell is then monitored or examined, with the inhibition of such translocation indicating that the test compound inhibits the binding of βarrestin to the phosphorylated μ opioid receptor. If desired, phosphorylation of the μ opioid receptor can be induced or enhanced by any suitable means, such as contacting a μ opioid receptor agonist such as morphine to the cell in an amount effective to induce phosphorylation (e.g., by adding the agonist to the culture medium or liquid medium in which the cell is contained). The cell is preferably a mammalian cell, but any suitable cell can be employed, including bacterial cells, yeast cells, fungal cells, plant cells, and other animal cells, so long as they express μ opioid receptor and phosphorylate, or can be induced to phosphorylate, the same, and contain the desired βarrestin protein coupled to an optically detectable molecule (e.g., either by exogenous introduction or expression of the βarrestin conjugate therein). Any suitable βarrestin may be employed as described above, with βarrestin-2 being preferred.

2. Test compounds. The present invention can be used with test compounds (or "probe molecules"), or libraries (where groups of different probe molecules are employed), of any type. In general, such probe molecules are organic compounds, including but not limited to oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, porphyrins, toxins, catalysts, as well as combinations thereof. Oligomers include peptides (that is, oligopeptides) and proteins, oligonucleotides (the term oligonucleotide also referred to simply as "nucleotide", herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

3. Pain control and active compounds. As noted above, the present invention provides a method of controlling pain in a subject, comprising inhibiting βarrestin binding to the phosphorylated μ opioid receptor in said subject in an amount effective to induce or enhance analgesia in the subject. The method may be carried out with or without concurrently administering a μ opioid receptor agonist such as morphine (or other opiate, as described below). When carried out without concurrent administration of μ opioid receptor, the analgesic activity relies upon the activity of endogenous opioid receptor agonists.

The inhibiting of βarrestin binding (preferably βarrestin-2 binding) to phosphorylated μ opioid receptor can be carried out directly or indirectly by any suitable means, including but not limited to knockout of the βarrestin gene as described herein, disabling or downregulating the kinase responsible for phosphorylation of the μ opioid receptor, administration of an antisense oligonucleotide that downregulates expression of the βarrestin, or the administration of an active compound that competitively inhibits binding of the βarrestin to phosphorylated μ opioid receptor (which may be identified by the assay techniques described above). Obviously, finctional μ opioid receptor itself must remain in the cells (particularly nerve cells) of the subject so that the primary analgesic activity of the μ opioid receptor agonist can be exerted.

Compounds produced or identified as active compounds by application of the assay procedures described herein to the test compounds or probe molecules described herein are useful in vitro and in vivo as μ opioid receptor agonists (in that they enhance the activity of opioids, although they do not bind to the same site as an opioid), are useful in enhancing the efficacy, potency, or analgesic activity of μ opioid receptor agonists. Such compounds are also useful in vivo in controlling pain in a subject in need thereof. By "controlling pain", "control of pain" and the like herein is meant partially or completely inhibiting a pain response or perception of pain in a subject, and/or partially or fully inducing local or general analgesia in a subject, either alone or in combination with another active agent administered to the subject such as a μ opioid receptor agonist (e.g., morphine). Subjects that may be treated by the compounds identified by the present invention include both human subjects and animal subjects (e.g., dogs, cats, horses, cattle) for veterinary purposes.

Thus, as noted above, further aspects of the present invention include active compounds produced or identified by the methods described hereinabove and pharmaceutical formulations of the same (e.g., said compound in a sterile pyrogen-free saline solution), along with the use of such compounds for the preparation of a medicament for the potentiation of the activity of μ opioid receptor agonists such as morphine, and/or for the control of pain, in a subject in need thereof, either alone or in combination with a μ opioid receptor agonist such as morphine.

In addition to morphine, other μ opioid receptor agonists, typically opiates, that may be used in conjunction with the present invention include, but are not limited to, codeine, oxycodeine, hydromorphone, diamorphine, methadone, fentanyl, sufentanil, buprenorphine, meperidine (Demerol®), etc.

The active compounds described above may be combined with a pharmaceutical carrier in accordance with known techniques to provide a pharmaceutical formulation useful carrying out the methods described above. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous), topical (i.e., both skin and mucosal surfaces), the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unitdose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such usefuil emulsifying agent is phosphatidyl choline.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The present invention is explained in greater detail in the following non-limiting Examples.

EXAMPLE 1

Production of βArrestin Knockout Mice

Because GPCRs, such as the substance P receptor and the opioid receptors, participate in processing the sensation of pain, we characterized analgesic responses through the μ opioid receptor (μOR) in mice lacking βarrestin-2. In the clinical setting, morphine is currently the most effective drug for alleviating intense and chronic pain. The antinociceptive (blocking of pain perception) actions of morphine are mediated through stimulation of the μOR, as demonstrated by the lack of morphine analgesia observed in knock out mice deficient in the μOR (H. Matthes et al., *Nature* 383, 819 (1996). B. Kieffer, *Trends Pharmacol Sci* 20, 19 (1999); I. Sora et al., *Proc Natl Acad Sci USA* 94, 1544 (1997)). Nevertheless, the neuronal signaling mechanisms mediating analgesia through HORs and morphine remain poorly understood. Moreover, the contribution of GPCR desensitization to the onset and duration of analgesia has been unclear.

βarrestin-2 knockout (βarr2-KO) mice were generated by inactivation of the gene by homologous recombination. A bacteriophage λ library of mouse 129SvJ genomic DNA (Stratagene, La Jolla, Calif.) was screened with the rat βarr2 cDNA (H. Attramadal et al., *J. Biol. Chem.* 267, 17882 (1992)). Positive phages were identified and analyzed by restriction digest. A 12-kb βarr2 fragment was digested with Bam HI, subcloned into pBluescript KS(–) and sequenced. The targeting vector was assembled by blunt-end ligation of a pHSV-TK cassette (from pIC19R/MCI-TK, M. R. Capecchi, University of Utah), a 2.8-kb Nco I-Bam HI βarr2 fragment, a pGK-neo cassette (from plasmid pD383, R. Hen, Columbia University) which replaced the 0.8-kb Bam HI-Hind III fragment of βarr2, and a 4.5 kb Hind III βarr2 fragment into pBluescript KS(−). This targeting vector was linearized with Not I and was electroporated into mouse embryonic stem cells. Genomic DNA from transfectants resistant to G418 and gancyclovir were isolated and screened by Southern (DNA) blot analysis using a 0.2 kb 5' external βarr2 probe and a 0.3 kb 3' external βarr2 probe. Chimeric animals were generated by microinjecting these ES cells into C57BL/6 blastocysts. Five chimeric male pups were obtained and mated with C57BL/6 females. Germline transmission was confirmed by Southern blotting. Heterozygous offspring were intercrossed to obtain homozygous mice. Wild-type and mutant mice used in this study were age-matched, 3 to 5 month old, male siblings. For protein immunoblot analysis, whole cell lysates were prepared by polytron homogenization in lysing buffer [10 mM Tris (pH 7.4), 5 mM EDTA, 1 protease inhibitor tablet/10 mL (Roche Molecular Biochemicals, Indianapolis, Ind. USA), 1% nonidet-40]. Polyacrylamide gels were loaded with 25 μg protein/lane and equivalent protein loading was confirmed by Ponceau S staining of the gels. After transfer to polyvinyldifluoride (PVDF) membranes, proteins were blotted with polyclonal antibodies to βarrestin-2 or βarrestin-1 [H. Attramadal et al., *J. Biol.Chem.*267, 17882 (1992)]. Bands were visualized with secondary antibody conjugated to horseradish peroxidase and an enhanced chemiluminescence detection system (Amersham, Piscataway, N.J.). All experiments were conducted in accordance with the NIH guidelines for the care and use of animals.

EXAMPLE 2

Identification of βArrestin Knockout Mice

Mice lacking βarrestin-2 were identified by Southern DNA blot analysis (FIG. 1A) and the absence of βarrestin-2 was confirmed by protein immunoblotting of extracts from brainstem, periaqueductal gray (PAG) tissue, spleen, lung and skin (FIG. 1B). Wild-type, heterozygous, and homozygous mutant mice had similar amounts of βarrestin-1 in the brain regions examined (FIG. 1B), arguing against compensatory up-regulation of βarrestin-1 in the absence of βarrestin-2. The βarr2-KO mice were viable and had no gross phenotypic abnormalities. However, after administration of morphine, obvious differences became apparent between the genotypes.

EXAMPLE 3

Evaluation of Morphine-Induced Antinociception in βarrestin Knockout Mice

Figure 2:
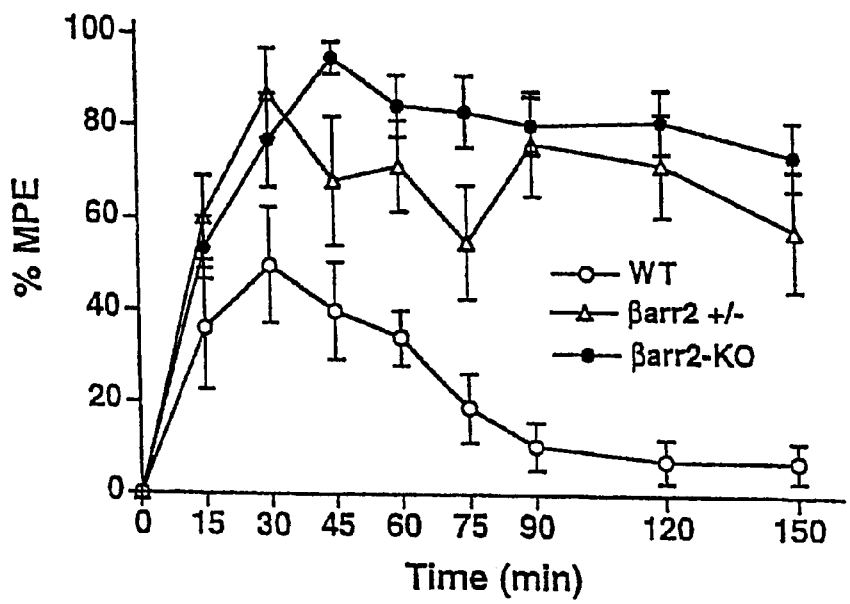
FIG. 2. Enhanced and prolonged morphine-induced antinociception in βarr2-KO mice. Antinociceptive responses were measured as hot plate (56° C.) response latency after morphine (10 mg/kg, s.c.) treatment. The "response" was defined by the animal either licking the fore- or hind-paws or flicking the hind-paws. In these studies, the most prominent response was fore-paw licking. To avoid tissue damage the animals were not exposed to the plate for more than 30 seconds. Data are reported as the percent of the maximal possible response time (30 seconds) which was determined from each individual mouse's basal response, the response after drug treatment, and the imposed maximum cutoff time with the following calculation (F. Porreca et al., *J Pharmacol Exp Ther* 230, 341 (1984); J. Belknap et al., *Physiol Behav* 46, 69 (1989). M. Gardmark et al., *Pharmacol Toxicol* 83, 252 (1998); G. Elmer et al., *Pain* 75, 129 (1998)): 100%×[(Drug response time−Basal response time)/(30 sec−Basal response time)]=% maximum possible effect (% MPE). WT (n=6), heterozygotes (+/−, n=5) and KO (n=9) mice were analyzed together in the same experiment. The % MPE curves of the βarr2-KO and βarr2+/−mice were significantly greater than the WT response curve (P<0.001) as determined by two-way ANOVA.

Morphine-induced antinociception was evaluated by measuring response latencies in the hot plate test. We used a dose of morphine (10 mg/kg) and route of administration (s.c.) well established to induce analgesia in many strains of mice (F. Porreca et al., *J Pharmacol Exp Ther* 230, 341 (1984). J. Belknap et al., *Physiol Behav* 46, 69 (1989). M. Gardmark et al., *Pharmacol Toxicol* 83, 252 (1998). G. Elmer et al., Pain 75, 129 (1998)). The analgesic effect of morphine was significantly potentiated and prolonged in the knockout mice as compared to that in their wild-type littermates (FIG. 2). Such robust responses to morphine were not only absent in the wild-type littermates (FIG. 2) but also in the parental mouse strains (C57BL/6 and 129SvJ) used to generate this knockout. Four hours after the morphine injection, βarr2-KO mice still exhibited significant analgesia (% maximum possible effect=31±0.4%); whereas, in control wild-type littermates, the analgesic effects of the same dose of morphine waned after about 90 minutes. βarr2 +/− mice were nearly as responsive to morphine as the βarr2-KO mice; however, this may reflect the imposed limit of the hot plate assay (30 sececonds), which is designed to prevent prolonged exposure of the mice to pain. Basal responses to the hot plate did not differ between genotypes (wild type: 6.2±0.3 sec., n=25; βarr2-KO: 6.1±0.4 sec., n=27). The differences in morphine-induced analgesia between the genotypes are unlikely to be due to pharmacokinetic differences in morphine metabolism, because the concentrations of morphine in blood, as determined by mass spectroscopy analysis, did not differ between wild type and βarr2-KO mice 2 hours after morphine injection (Mice were injected with morphine (10 mg/kg, subcutaneous). After 30 minutes or 2 hours, wild-type mice were killed and blood was collected in vials containing sodium-fluoride and potassium-oxalate. Morphine concentration in blood samples pooled from 3 mice per sample were 1,500 ng/mL after 30 min., and 83 ng/mL blood after 2 hours as measured by mass spectroscopy analysis [Occupational Testing Division of LabCorp, Inc., Research Triangle Park, North Carolina, USA]. In similar experiments, βarr2-KO mice had a concentration of 93 ng/mL in the blood after 2 hours).

EXAMPLE 4

Evaluation of Low Dosage Morphine in βarrestin Knockout Mice

Figure 3:
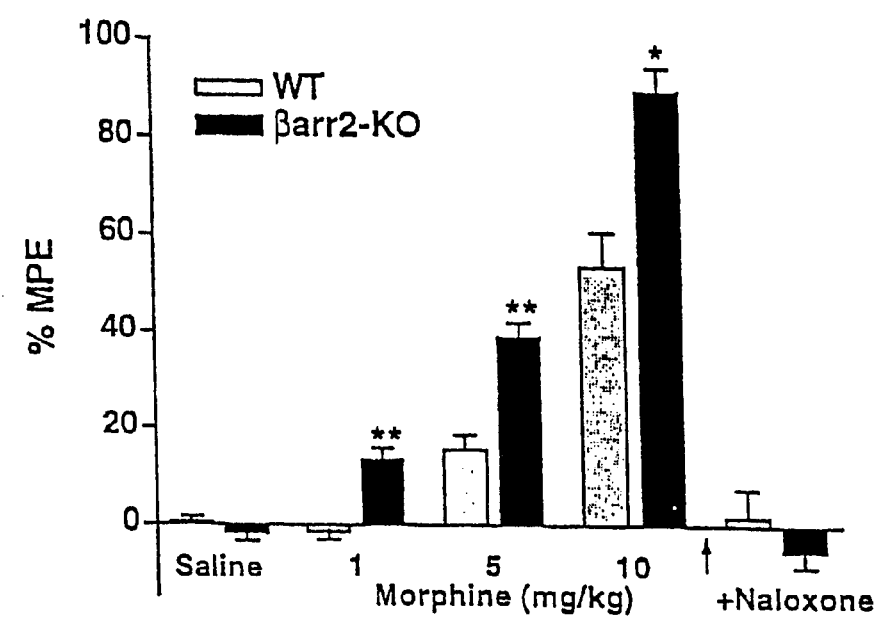
FIG. 3. Greater dose-dependent antinociceptive responses to morphine in βarr2-KO mice. The degree of antinociception was determined by measuring latency of hot plate (56° C.) responses (FIG. 2). Withdrawal latencies were measured 30 min. after a first dose of morphine (1 mg/kg, s.c.) at which point, animals were immediately injected with 4 mg/kg, s.c. morphine for a cumulative dose of 5 mg/kg. Antinociception was again assessed after 30 min. and mice were immediately injected with morphine (5 mg/kg, s.c.), to give a final cumulative dose of 10 mg/kg. Withdrawal latencies were again measured after 30 min. after which, mice were immediately injected with naloxone (2.5 mg/kg, s.c.). After 10 min., antinociception was assessed once more. WT (n=7) and βarr2-KO (n=6) mice were significantly different at each dose (*P<0.01, **P<0.001; Student's t-test). Means±S.E.M. are shown. In an additional experiment, morphine (25 mg/kg, s.c.) induced the maximum imposed response (100%) in both genotypes. Thus, an approximate 2 fold shift in the apparent $ED_{50}$ values was observed between genotypes [WT: 9.77 (8.08–11.81) mg/kg; KO: 5.98 (5.10–6.94) mg/kg (95% confidence intervals)].

Lower doses of morphine were also tested in these assays. Even at doses of morphine (1 mg/kg, s.c.) that were subanalgesic in wild type mice, βarr2-KO animals displayed a significant increase in their nociceptive thresholds (FIG. 3). At 30 minute intervals, immediately following the antinociception test, mice were given repeated cumulative doses of morphine resulting in final concentrations of 5, and 10 mg/kg (I. Sora et al., *Proc Natl Acad Sci USA* 94, 1544 (1997)). At the highest cumulative dose, mice reached similar levels of antinociception as seen in FIG. 2, in which this amount of morphine was administered in a single injection. At every dose, the βarr2-KO animals experienced greater antinociception after morphine treatment than did their wild-type littermates.

EXAMPLE 5

Evaluation of Morphine Antagonists in βarrestin Knockout Mice

To test whether the analgesic effects of morphine were mediated by actions at the μOR, mice were treated with various antagonists. Naloxone (2.5 mg/kg, subcutaneous injection) which immediately reverses the effects of opiates, was given 30 minutes after morphine (10 mg/kg). Naltrindole [P. Portoghese et al., *J. Med. Chem.* 88, 1547 (1990)] was given 20 minutes before morphine, and nor-binaltorphimine (A. Takemori et al., *J Pharmacol Exp Ther* 246, 255 (1988)) was given 1 hour before morphine (H. Matthes et al., *J Neurosci* 18, 7285 (1998)).

Naloxone, a well-established OR antagonist, was administered to the same mice, immediately after measuring the antinociceptive effects of morphine (10 mg/kg). Naloxone (2.5 mg/kg, s.c.) completely reversed the effects of morphine in both the wild-type and βarr2-KO animals within 10 minutes. However, the δ and κ OR-selective antagonists naltrindole (2.5 mg/kg, s.c.) and nor-binaltorphimine (5 mg/kg s.c.) did not inhibit analgesia in wild type nor βarr2-KO mice (data not shown). The morphine dose dependency of the antinociceptive response and the reversal of the effects with naloxone suggest that the potentiated and prolonged effects in mice that lack βarrestin-2 result from stimulation of the μOR.

EXAMPLE 6

Body Temperature Measurements in Wild-Type and βarrestin Knockout Mice

Figure 4:
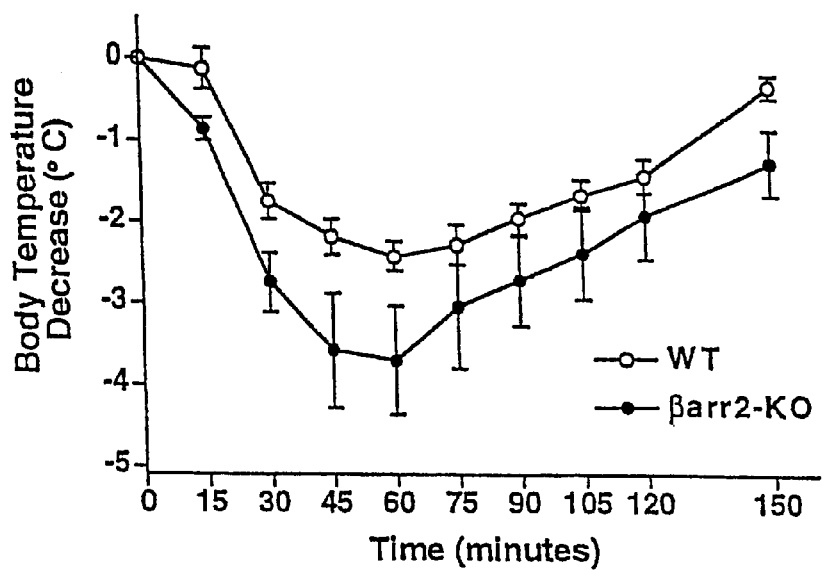
FIG. 4. Increased hypothermic responses to morphine in βarr2-KO mice. Rectal body temperatures were measured with a digital thermometer (M. Adler et al., *Annu Rev Pharmacol Toxicol* 28, 429 (1988); F. Fumagalli et al., *J Neurosci* 18, 4861 (1998) (TH8, Physitemp, Clifton, N.J., USA). The probe was inserted into the rectum and maintained until the temperature reading stabilized. Basal body temperatures did not vary significantly between genotypes (WT: 36.4±0.1° C.; KO: 36.8±0.1° C.). WT (n=5) and KO (n=5) animals were analyzed in parallel during the same experiment. The curves are significantly different (P<0.001) as determined by 2-way ANOVA. Means±S.E.M. are shown.

Wild-type and βarr2-KO mice were also evaluated for changes in body temperature (M. Adler et al., *Annu Rev Pharmacol Toxicol* 28, 429 (1988). Rectal body temperatures were determined with a digital thermometer [F. Fumagalli et al., *J Neurosci* 18, 4861 (1998)] (TH8, Physitemp, Clifton, N.J., USA). The probe was inserted into the rectum and maintained until the temperature reading stabilized). No significant differences in basal body temperature were found between genotypes, however βarr2-KO mice experienced a greater drop in body temperature after morphine treatment than did wild-type (FIG. 4). This greater decrease in temperature also persisted longer than that in their wild type littermate controls.

EXAMPLE 7

Radioligand Binding Assays

To investigate whether the μOR population was altered in the KO mice, radioligand binding analysis on membranes prepared from different brain regions was performed.

Brain regions were dissected and immediately frozen in liquid nitrogen and were stored at −80° C. for less than 1 week before use. Samples were placed on ice and homogenized by polytron in membrane preparation buffer [50 mM Tris (pH 7.4), 1 mM EDTA, 3 mM MgCl$_2$] and crude membranes were prepared by centrifugation at 20,000×g for 15 min at 4° C. Membranes were resuspended in either 50 mM Tris-HCl (pH 7.4) for radioligand binding assays or in assay buffer [50 mM Tris-HCl (pH 7.4), 100 mM NaCl, 3 mM MgCl2, 0.2 mM EDTA] containing 10 μM GDP for [$^{35}$S]GTYPγS binding assays. For both binding assays, reactions were terminated by rapid filtration over GF/B filters (Brandel, Inc., Gaithersburg, Md.) using a Brandel cell harvester (Brandel, Inc., Gaithersburg, Md.). Filters were washed 3 times with ice cold 10 mM Tris-HCl (pH 7.4) and then counted in a liquid scintillation counter. Hypothalamus, brain stem, and periaqueductal gray (PAG) regions were chosen because they contain μORs and are implicated in the regulation of pain and body temperature (D. Mayer and D. Price, *Pain* 2, 379 (1976). T. Yaksh et al., *Prog Brain Res* 77, 371 (1988). D. J. Smith, et al., *Eur J Pharmacol* 156, 47 (1988)). Data are given in Table 1. Saturation binding studies with $^3$H-naloxone, at concentrations that preferentially label the μOR, revealed a single high affinity binding site, which represents the μOR. The number and affinity of μORs did not significantly differ between the two genotypes in any of the brain regions examined.

TABLE 1

$^3$H-Naloxone binding in brain regions of Wild Type and Knockout mice.[1]

| Brain region | Wild Type | | βarr2-Knockout | |
|---|---|---|---|---|
| | B$_{MAX}$ (fmol/mg) | K$_D$ (nM) | B$_{MAX}$ (fmol/mg) | K$_D$ (nM) |
| PAG | 132 ± 9 | 4.0 ± 0.1 | 144 ± 13 | 4.5 ± 0.8 |
| Brainstem | 49 ± 7 | 1.5 ± 0.2 | 54 ± 9 | 3.0 ± 0.8 |
| Hpothalamus | 103 ± 18 | 6.2 ± 1.6 | 89 ± 8 | 3.8 ± 0.2 |

[1]Saturation binding assays were performed on membranes from different brain regions (50–100 μg/tube) with increasing concentrations of $^3$H-naloxone (0–12 nM, 52.5 Ci/mmol, Amersham, Piscataway, New Jersey, USA). Nonspecific binding was determined in the presence of 10 μM naloxone. Membranes were incubated at 25° C. for 1 hour. Binding parameters were determined via Scatchard analysis of specific binding. Data are the mean ± S.E.M. of 3–4 experiments performed in duplicate.

Figure 5:
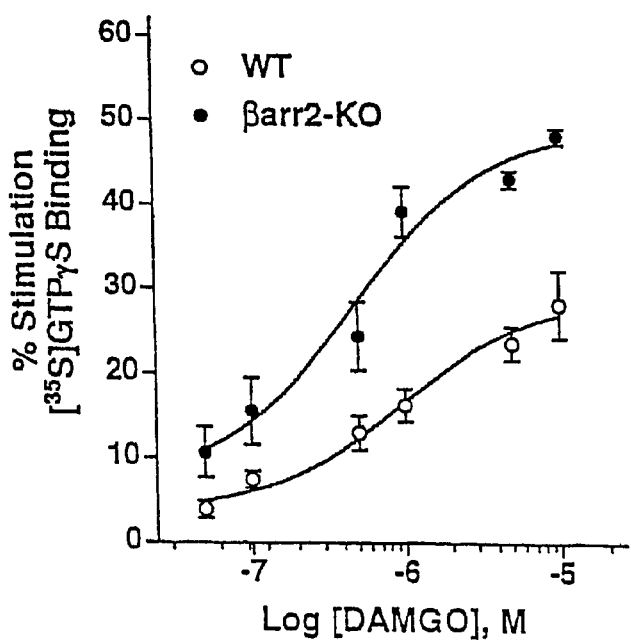
FIG. 5. Binding of [$^{35}$S]GTPγS to periaqueductal gray membranes from βarr2-KO and wild type (WT) mice. [$^{35}$S]GTPγS binding to isolated periaqueductal gray (PAG) membranes (prepared as described in conjunction with Table 1 below) was determined after 2 hour stimulation (30° C.) with 50–10,000 nM of the mOR-selective agonist, [D-Ala2, MePhe4, Gly5-ol]enkephalin (DAMGO). PAG membranes (10 µg protein per assay tube) were incubated in the presence of 10 µM GDP and 50 pM [$^{35}$S]GTPγS (1250 Ci/mmol, NEN, Boston, Mass.). [$^{35}$S]GTPγS binding was measured as described (P. Portoghese, in *Handbook of Experimental Pharmacology. Opioids I*, A. Herz, Ed. (Springer-Verlag, New York, 1993) p.p. 279–293. A. et al., ibid., p.p. 645–679). [$^{35}$S]GTPγS binding is expressed as percent increase in [$^{35}$S]GTPγS binding relative to binding in unstimulated samples. Data were analyzed by nonlinear regression using GraphPad Prism software and are presented as the mean±S.E.M of at least three experiments performed in triplicate wherein WT and βarr2-KO brain regions were assayed simultaneously. In the absence of agonist stimulation, basal [$^{35}$S]GTPγS binding was: WT: 440±83 cpm and βarr2-KO: 527±99 cpm.

Additional evidence for increased sensitivity of the μOR in βarr2-KO animals was obtained in biochemical experiments. We measured agonist-stimulated binding of [$^{35}$S] GTYPγS to G proteins in isolated membranes the most proximal manifestation of GPCR activation (D. Selley et al., *Mol Pharmacol* 51, 87 (1997)). Because morphine acts in vitro to stimulate μ, δ, and κ opioid receptors, the μOR-selective agonist, [D-Ala$^2$, MePhe$^4$, Gly$^5$-ol]enkephalin (DAMGO), was used to specifically activate G protein coupling to μORs. DAMGO stimulated more [$^{35}$S]GTYPγS binding in membranes derived from βarr2-KO mice than in those derived from wild-type littermates (FIG. 5). Similar results were also obtained in brainstem membranes (data not shown). The amount of Gα proteins (G$_{i/o/z}$) as determined by protein immunoblotting, did not vary between the genotypes (data not shown). These observations suggest that there is enhanced coupling of μORs to G proteins in tissues derived from βarr2-KO mice. Although the enhanced analgesia induced by morphine may involve complex neurological signaling, this biochemical evidence supports the interpretation that the enhanced physiological responsiveness in the knockout animals results from increased sensitivity of signaling by the μOR.

These studies demonstrate in an animal model that the absence of βarrestin-2 can affect the efficacy of GPCR activation. In transfected cultured cells, the degree of β$_2$-adrenergic receptor signaling is dependent upon the cellular complement of GRK2 and GRK3 and βarrestins (L. Menard et al., *Mol Pharmacol* 51, 800 (1997); S. Mundell et al., *Biochemistry* 38, 8723 (1999)). These observations, along with those presented here, directly support the proposed role of βarrestin-2 in preventing further receptor-G protein coupling and mediating desensitization of the GPCR. Moreover, βarrestins are not only involved in the dampening of GPCR responsiveness after agonist stimulation, but also influence the sensitivity of the response.

The simplest interpretation of these results is that μOR signaling is regulated by βarrestin-2. However, in transfected cells, morphine fails to induce the internalization of the μOR and a GFP-tagged βarrestin-2 fails to translocate to μOR overexpressed in cell culture upon exposure to morphine (J. Arden et al., *J Neurochem* 65, 1636 (1995). D. Keith et al., *J Biol Chem* 271, 19021 (1996); J. Whistler and M. von Zastrow, *Proc Natl Acad Sci USA* 95, 9914 (1998); J. Zhang et al., *Proc Natl Acad Sci USA* 95, 7157 (1998)). Interestingly, these in vitro studies have been conducted with the rat μOR or the mouse MOR1 which are not particularly rich in potential phosphorylation sites. Several splice variants of the μOR are present in mouse brain that contain several potential phosphorylation sites (Y. Pan et at., *Mol Pharmacol* 56, 396 (1999)). Some of these isoforms can contribute to morphine-induced analgesia. The involvement of these receptors might explain the differences between the in vitro studies and those with the βarr2-KO mice.

The βarr2-KO mice were very similar in phenotype to their wild type littermates and other GPCR-directed drugs did not necessarily elicit different responses between the genotypes. For example, locomotor responses to dopamine receptor stimulation by cocaine and apomorphine were not enhanced (data not shown). These observations suggest that various GPCRs are differentially affected by the loss of βarrestin-2. Other regulatory elements, such as GRKs or βarrestin-1, could compensate for the lack of βarrestin-2, or the receptors could vary in their requirement for βarrestin interaction for their regulation.

The foregoing is illustrative of the present invention, and is not to be construed as limiting thereof. The invention is defined by the following claims, with equivalents of the claims to be included therein.

That which is claimed is:

1. An in vitro method of screening a compound for activity in controlling pain, wherein the method comprises:
   (a) providing a cell that expresses a μ opioid receptor, a G protein coupled receptor kinase, and that contains a conjugate comprising a βarrestin and an optically detectable molecule;
   (b) exposing the cell to the compound;
   (c) exposing the cell to an agonist for the μ opioid receptor; and
   (d) monitoring for inhibition of βarrestin binding to the phosphorylated μ opioid receptor, the inhibition of such binding by said compound indicating said compound may be active in controlling pain.

2. A method according to claim 1, wherein said βarrestin is βarrestin 2.

3. An in vitro method of screening a compound for activity in potentiating μ opioid receptor agonist activity, wherein the method comprises:
   (a) providing a cell that expresses a μ opioid receptor, a G protein coupled receptor kinase, and that contains a conjugate comprising a βarrestin and an optically detectable molecule;
   (b) exposing the cell to the compound;
   (c) exposing the cell to an agonist for the μ opioid receptor; and
   (d) monitoring for inhibition of βarrestin binding to the phosphorylated μ opioid receptor;
   the inhibition of such binding by said compound indicating said compound is active in potentiating μ opioid receptor agonist activity.

4. A method according to claim 3, wherein said βarrestin is βarrestin 2.

5. A method according to claim 3, wherein said μ opioid receptor agonist is selected from the group consisting of morphine, codeine, oxycodeine, hydromorphone, diamorphine, methadone, fentanyl, sufentanil, buprenorphine, and meperidine.

6. A method according to claim 3, wherein said μ opioid receptor agonist is morphine.

7. An in vitro method of screening a compound for activity in controlling pain, wherein the method comprises:
   (a) providing a cell that expresses a μ opioid receptor, a G protein coupled receptor kinase, and that contains a conjugate comprising an arrestin and an optically detectable molecule;
   (b) exposing the cell to the compound;
   (c) exposing the cell to an agonist for the μ opioid receptor; and
   (d) monitoring for inhibition of one or more of the following, inhibition indicating that the compound may be active in controlling pain:
      (i) translocation of the arrestin to the phosphorylated μ opioid receptor; or
      (ii) binding of the arrestin to the phosphorylated μ opioid receptor.

8. A method according to claim 7, wherein the arrestin is βarrestin.

9. An in vitro method of screening a compound for activity in controlling pain, wherein the method comprises determining whether or not the compound inhibits at least one of the following, the inhibition of one or more of the following indicating that the compound may be active in controlling pain:
   (a) arrestin translocation to phosphorylated μ opioid receptors;
   (b) arrestin binding to phosphorylated μ opioid receptors; or
   (c) GRK phosphorylation of μ opioid receptors.

10. An in vitro method of screening a compound for activity in potentiating μ opioid receptor agonist activity, wherein the method comprises:
    (a) providing a cell that expresses a μ opioid receptor, a G protein coupled receptor kinase, and that contains a conjugate comprising an arrestin and an optically detectable molecule;
    (b) exposing the cell to the compound;
    (c) exposing the cell to an agonist for the μ opioid receptor; and
    (d) monitoring for inhibition of one or more of the following, inhibition indicating that the compound is active in potentiating μ opioid receptor agonist activity:
       (i) translocation of the arrestin to the phosphorylated μ opioid receptor; or
       (ii) binding of the arrestin to the phosphorylated μ opioid receptor.

11. A method according to claim 10, wherein the arrestin is βarrestin.

12. A method according to claims 10, wherein said μ opioid receptor agonist is selected from the group consisting of morphine, codeine, oxycodeine, hydromorphone, diamorphine, methadone, fentanyl, sufentanil, buprenorphine, and meperidine.

* * * * *